United States Patent [19]
Woodman

[11] Patent Number: 5,718,672
[45] Date of Patent: Feb. 17, 1998

[54] DYNAMIC HIP SPLINT

[75] Inventor: Lynda M. Woodman, Oakdale, Minn.

[73] Assignee: Gillette Children's Hospital, St. Paul, Minn.

[21] Appl. No.: 735,644

[22] Filed: Oct. 23, 1996

[51] Int. Cl.$^6$ ................................................ A61F 5/01
[52] U.S. Cl. ................................................ 602/23; 602/5
[58] Field of Search ................................ 602/5, 23–25; 128/869, 878, 882–883

[56] References Cited

U.S. PATENT DOCUMENTS

| | | | |
|---|---|---|---|
| 2,245,293 | 6/1941 | Ogburn | 128/882 X |
| 2,650,590 | 9/1953 | Moore et al. | 128/882 |
| 3,815,589 | 6/1974 | Bosley | 602/24 |
| 4,203,433 | 5/1980 | Prahl | 602/24 |
| 5,076,288 | 12/1991 | Millard et al. | 128/878 X |
| 5,558,628 | 9/1996 | Bzoch . | |

Primary Examiner—Richard J. Apley
Assistant Examiner—Victor K. Hwang
Attorney, Agent, or Firm—Gregory F. Cotterell

[57] ABSTRACT

A dynamic hip splint for attaching to opposing thighs of a patient for correcting chronic abduction and external rotation of the patient's hips, the splint comprising a first thigh cuff positionable onto a thigh of the patient, a second thigh cuff positionable onto the opposite thigh of the patient and an elastic band interconnecting between the first and second thigh cuffs for urging the first and second thigh cuffs towards one another such that when the first and second thigh cuffs are positioned on a patient's thighs, the elastic band urging the first and second thigh cuffs towards each other results in adduction and internal rotation of the hips of the patient to a more neutral anatomic position. This more neutral position in adduction and internal rotation facilitates delivery of routine cares to the patient and also improves gait training and mobility for those patients suffering from malpositioning of the lower extremities secondary to a neuro-muscular abnormality.

10 Claims, 2 Drawing Sheets

DYNAMIC HIP SPLINT

FIELD OF THE INVENTION

This invention relates to the splinting of human limbs and in particular to a dynamic elastic hip splint positionable on the patient's thighs interconnecting the two thighs for supporting the legs in adduction and internal rotation.

BACKGROUND OF THE INVENTION

A number of unfortunate children are born each year with neuromuscular congenital abnormalities. A portion of these children are anatomically normal but suffer from abnormal muscular tone. The abnormal tone may manifest itself as hypertonic or hypotonic, with both having a subset of hypermobility.

The hip is a ball and socket joint having motion in three axes. Normal skeletal development in general, and more specifically the hip joint, is directly dependent on proper positioning of the femoral head proximate the acetabulum and motion of the joint in all three axes of motion, with load bearing stresses carried through the joint from femur to the pelvis. The first axis is the front to back orientation generally referred to as extension (to the back) and flexion (toward the front). The second axis is lateral to medial, generally referred to as abduction (extending the hip in the lateral direction) and adduction (extending the hip medially so the leg approaches the other leg). The third axis is rotation, with external rotation being that motion where the anterior portion of the leg moves laterally, and internal rotation evidenced by rotating the anterior portion of the leg medially.

Development of the hip begins in utero and continues over approximately the first eight years of a child's life. With normal growth and development, compressive forces, from first crawling then walking, transmit through the hip from femur to pelvis gradually increasing acetabular depth which in turn contributes to formation of the femoral head into its appropriately round shape. This cooperative development continues until normal acetabular depth is reached at about age eight. In order to begin to walk normally, a toddler must achieve sufficient strength and control to be able to achieve hip extension and flexion while bearing their own weight and maintaining a neutral positioning with regard to abduction/adduction and internal/external rotation.

For a substantial number of children with neuro-muscular abnormalities causing or contributing to abnormal muscular tone, hip motion is not well controlled. Whether the neuromuscular abnormality is due to hypertonicity, spasticity or hypotonicity, the resulting anatomical orientation finds the hips in positions of abduction, external rotation and flexion. Control for many of these children often is so poor as to allow this abnormal positioning to interfere with the child's ability to even roll over. Consequently, what little acetabular or femoral head development could be anticipated, goes unrealized in many of these children secondary to this persistent abnormal positioning. If these children do not receive help before the age of eight when hip development ceases, then subsequent attempts to rehabilitate or train these children at a later age will be exacerbated because of the generally poor or lacking hip development. Two common complications from poorly developed hips are chronic subluxation and dislocation. If there is to be any hip joint development at all, intervention must begin at a very early age and be carried on for a number of years, preferably through age eight.

Abnormal positioning in these patients also leads to atypical pressures around the hip joint which further deforms the component parts of the hip increasing the likelihood of difficulties later, including attempts to rehabilitate the older child when they are finally stronger. Poor development of the acetabulum and femoral head coupled with actual deformation of these components leads to abnormal joint motion also complicating the neuromuscular abnormality. Additionally, deformations and abnormal stresses to the deformed structures increases the likelihood of subluxation and/or complete dislocation of the hip joints adding additional complication to an already difficult existence.

Past clinical practice has been to use a loop of material either elastic or non-elastic such as a foam strap, nylon stocking or ACE® wrap and binding the patient's legs together in order to counteract the tendency for abduction and external rotation. Such devices allow some dynamic motion, but these devices are only temporary, not easily reproducible day to day. Additionally, the devices did little else other than to conveniently position the legs to assist attendants for either turning the patient or transferring the patient from bed to wheelchair or other similar apparatus. Unfortunately, such devices and methods do not provide for facilitating rehabilitation of the patient. If femoral head growth and acetabular formation are to occur, there must be additional means by which the patient will be facilitated to not only assume a more neutral position but also begin to bear weight and maneuver the hips through a definite range of motion suitable for bearing weight and walking.

There is a definite need for a device and method of interventional treatment to provide these unfortunate children with a more neutral hip joint alignment that still provides for active hip motion.

SUMMARY OF THE INVENTION

The present invention discloses a dynamic hip splint for attaching to opposing thighs of a patient for correcting chronic abduction and external rotation of the patient's hips, the splint comprising a first thigh cuff positionable onto a thigh of the patient, a second thigh cuff positionable onto the opposite thigh of the patient, and an elastic band interconnecting between the first and second thigh cuffs for elastically urging the first and second thigh cuffs towards one another such that when the first and second thigh cuffs are positioned on a patient's thighs, the elastic band urging the first and second thigh cuffs towards each other results in adduction and internal rotation of the hips of the patient to a more, or nearly so, neutral anatomic position in these two of the three axes of motion.

A preferred embodiment of the present invention discloses a dynamic hip splint for attaching to opposing thighs of a patient for correcting chronic abduction and external rotation of the patient's hips, the splint comprising a first adjustable thigh cuff and a second adjustable thigh cuff, each cuff positionable opposite the other on, and enclosable around, respective right and left thighs of the patient, and each cuff having two opposite free ends and a mid section therebetween, with each mid section positionable proximate the medial aspect of the respective thigh it encloses, the mid section of each cuff having a front portion and a back portion and a closure mechanism for attaching the two free ends of each cuff to each other thereby enclosing each cuff around its respective thigh of the patient, an elastic band, interconnecting between the first and second adjustable thigh cuffs for urging the first and second adjustable thigh cuffs towards one another, the elastic band having four limbs extending from a single locus, each limb having a free end, a first limb free end for attaching to the front portion of the first cuff, a second limb free end for attaching to the back portion of the first cuff, a third limb free end for attaching to the front portion of the second cuff, and a fourth limb free end for attaching to the back portion of the second cuff, and an adjustable attachment mechanism for attaching each of the four limb free ends to each respective front and back portions such that when the first and second adjustable thigh cuffs are positioned on a patient's thighs, the elastic band urging the first and second adjustable thigh cuffs towards each other results in adduction and internal rotation of the hips of the patient to a more neutral anatomic position.

Other objects of the present invention and many of the attendant advantages of the present invention will be readily appreciated as the same become better understood by reference to the following detailed description when considered in connection with the accompanying drawings.

DETAILED DESCRIPTION OF THE INVENTION

Figure 1:
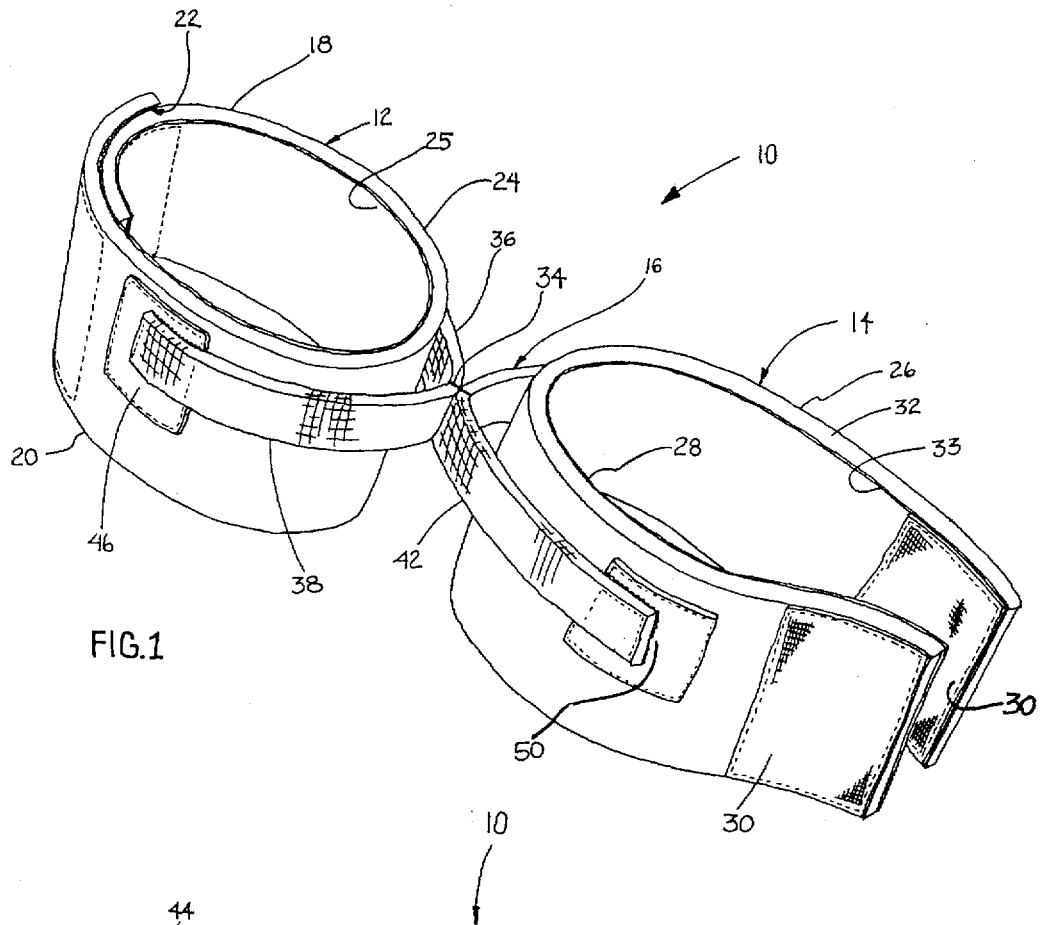
FIG. 1 is a perspective view of an embodiment of the present invention.
Figure 2:
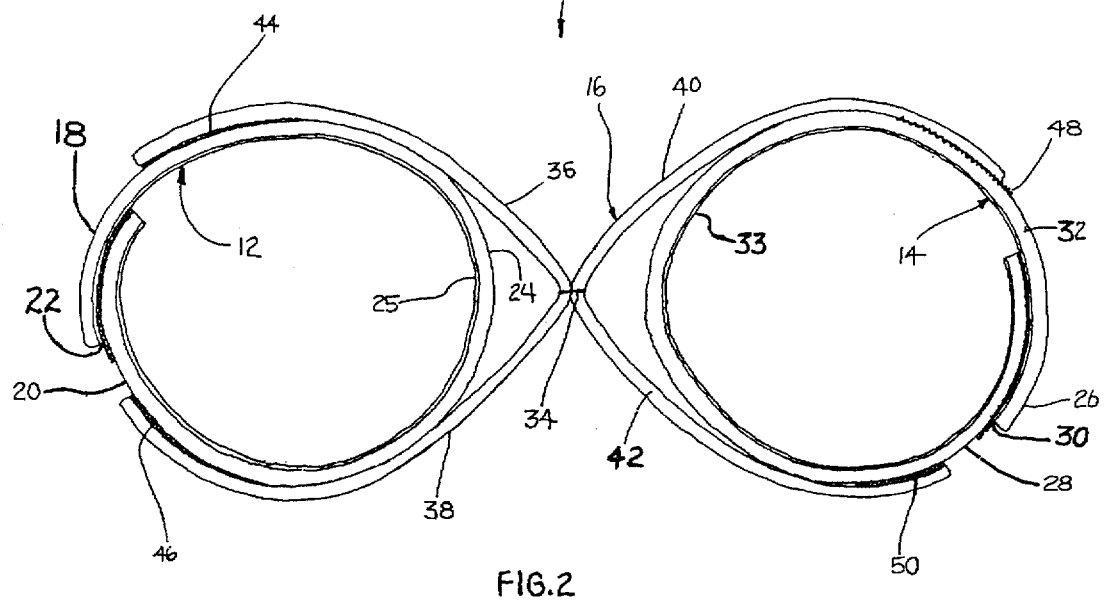
FIG. 2 is a top plan view of the embodiment depicted in FIG. 1.

As shown in FIGS. 1 and 2, there is disclosed an embodiment of a dynamic hip splint 10 comprising a right cuff assembly 12, a left cuff assembly 14, and an elastic band 16 interconnecting between right cuff assembly 12 and left cuff assembly 14. It should be understood that the use of right and left with this description is in reference to a patient's right and left. Additionally, it should be understood that this use of right and left is for convenience only in organizing the disclosure. The present invention, as disclosed herein, has cuffs and interconnecting elastic band that are interchangeable right with left, front with back, this being a useful characteristic for ease of placing the dynamic hip splint on a patient.

Right cuff assembly 12 includes a posterior cuff portion 18, an anterior cuff portion 20 and a closure mechanism 22 between posterior cuff portion 18 and anterior cuff portion 20. Left cuff assembly 14 further includes a posterior cuff portion 26, an anterior cuff portion 28, and a closure mechanism 30 between posterior cuff portion 26 and anterior cuff portion 28.

Elastic band 16 includes a locus or a common junction 34, a right posterior limb 36, a right anterior limb 38, a left prosthetic limb 40, and a left anterior limb 42. Elastic band 16 interconnects between the right cuff assembly 12 and left cuff assembly 14 through a right posterior attachment site 44, a right anterior attachment site 46, a left posterior attachment site 48, and a left anterior attachment site 50. Attachment site 44 interconnects right posterior limb 36 with posterior cuff portion 18. Attachment site 46 attaches right anterior limb 38 to anterior cuff portion 20. Left posterior attachment site 48 attaches left posterior limb 40 to posterior cuff portion 26. Attachment site 50 attaches left anterior limb 42 to anterior cuff portion 28. Each of attachment sites 44, 46, 48, and 50 includes complimentary attaching surfaces that work in concert with one another and are carried on the respective cuff portion and free end of each elastic band limb.

Right cuff assembly 12 is openable and closeable at closure mechanism 22 whereby the free end of anterior cuff portion 20 is positioned proximate the free end of posterior cuff portion 18 engaging closure mechanism 22. A similar mechanism is used for left cuff assembly 14 having a closure mechanism 30. Closure mechanisms 22 and 30 include complimentary closure surfaces that work in concert with one another and are carried on the respective cuff portions.

Right cuff assembly 12 and left cuff assembly 14 may be constructed using a number of materials such as cotton and wool cloth, felt, and a number of synthetic resilient polymeric compounds such as nylon, polyethylene, polyester, and polypropylene in weaves as fabrics or as foams in a web strip configuration. In a preferred embodiment, right cuff assembly 12 and left cuff assembly 14 are constructed with closed cell foam 24, 32 respectively and using an inner fabric liner 25, 33 respectively. The foam is preferably neoprene with a fabric liner such as a synthetic fabric made with nylon. A suitable neoprene product with a terry inner liner may be obtained from Berik Corporation, Silverdale, Wash.

Closure mechanisms 22 and 30 along with attachment sites 44, 46, 48, and 50 may use a number of different means for closure such as snap, buckles, hooks and loops and buttons. The common salient feature of all of these various closure mechanisms is that they provide a range of closure positions so that a single dynamic hip splint device may be usable on a variety of different sized children or, in the alternative, on the same child but adaptable to accommodate the child's growth. In a preferred embodiment, these closure and attachment mechanisms use Velcro® hook and loop material. The widest range of sizing and positioning control is provided by the Velcro® material.

A useful alternative embodiment is to substitute sewing for right posterior attachment site 44 and left posterior attachment site 48. Sewing the free end of right posterior limb 36 to posterior cuff portion 18, and sewing the free end of left posterior limb 40 to posterior cuff portion 26 provides for easier application of the device to the patient and decreases the likelihood of losing a component.

Elastic band 16 may be constructed from a number of elastic materials and in the preferred embodiment the elastic band is constructed from an elastic mesh cotton fabric and rubber strands in an elastic weave. The present invention also anticipates the usefulness of elastic bands of various elastic strengths to accommodate the patient as they grow and become stronger. A suitable prosthetic elastic band may be obtained under the product name Elastic H. D. Webbing through Knit-Rite, Kansas City, Mo. This elastic is available in several different widths and strengths.

Figure 3:
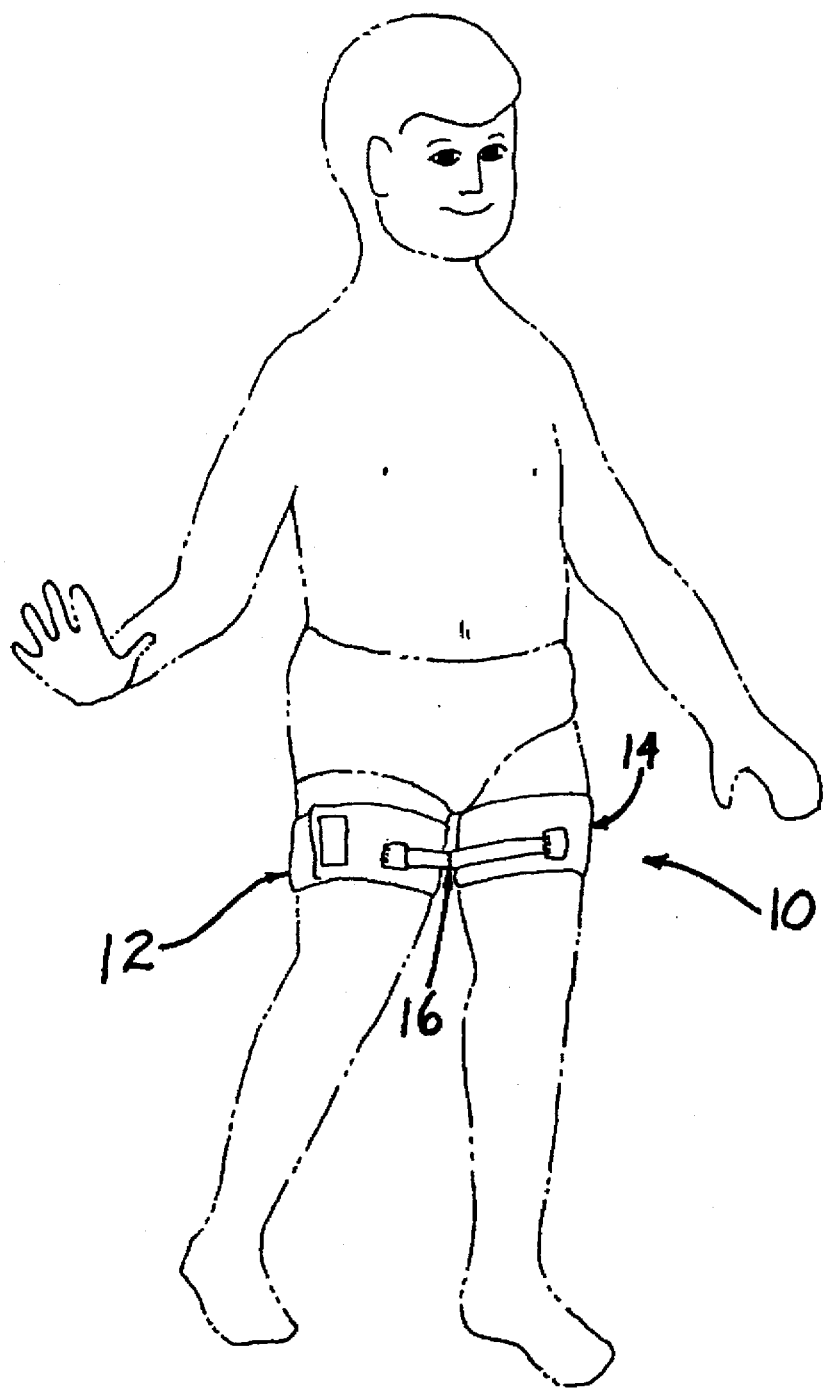
FIG. 3 is a perspective view of the embodiment depicted in FIG. 1 as applied to a patient, shown in phantom.

In operation, in reference to FIGS. 1 through 3, after appropriate patient selection, dynamic hip splint 10 is placed on the thighs of a patient by first placing right cuff assembly 12 around the thigh at approximately the mid-thigh level so that anterior cuff portion 20 is placed, with liner 25 against the skin of the patient's thigh, from in front and posterior cuff portion 18 is brought around to overlap anterior cuff portion 20 in the region of closure mechanism 22 to provide a snug, yet comfortable fit of right cuff assembly 12 to the patient's right thigh.

In like fashion, left cuff assembly 14 is positioned on to the thigh of the patient at approximately the mid-thigh level with anterior cuff portion 28 placed anteriorly, with liner 33 against the patient's skin, and posterior cuff portion 26 is brought around from the rear so as to overlap anterior cuff portion 28 in the region of closure mechanism 30 to provide a snug, yet comfortable fit of left cuff assembly 14 to the left thigh.

The patient's legs are then internally rotated and adducted until the patient's legs reach an approximate neutral position in respect to the long axis of the thighs suitable for bearing weight in an upright manner. Conversely, having the legs at a neutral position may be convenient solely for the purpose of constraining the legs to an internally rotated and adducted position to facilitate administering daily cares to the patient such as rolling the patient, or the patient, or transferring the patient from one support structure, such as a bed, to another, such as a wheelchair.

While holding the legs in this approximately neutral position, elastic band 16 is placed between right cuff assembly 12 and left cuff assembly 14 so that the free end of right posterior limb 36 is positioned adjacent right posterior attachment site 44. The free end of right anterior limb 38 is positioned adjacent right anterior attachment site 46. The free end of left posterior limb 40 is positioned adjacent left posterior attachment site 48. Finally, the free end of left anterior limb 42 is positioned adjacent left anterior attachment site 50. Attachment of these four limbs to their respective attachment sites accomplishes the restraining of the legs in roughly a neutral position as desired by the caregiver.

It should be apparent to one skilled in the art, that the total amount of adduction and internal rotation is controllable by carrying out repositioning &each of the four limbs of elastic band 16. By way of example, internal rotation may be increased by repositioning the free ends of right anterior limb 38 and left anterior limb 42 farther lateral on their respective attachment sites 46 and 50. The degree of adduction may be altered by readjusting anterior and posterior attachment sites on either the right cuff assembly 12 or left cuff assembly 14 or by adjusting all four limbs to both cuff assemblies 12 and 14. Alternatively, if the two posterior bands 36 and 40 are sewn to their respective posterior cuff portions 18 and 26, the ability to control adduction and internal rotation is limited to adjusting placement of the two anterior bands 38 and 42.

The caregiver may now release their hold on the patient's legs and allow dynamic hip splint 10 to assume the role of maintaining a dynamic internal rotation and adduction of the hips. Any amount of external rotation and/or abduction attempted by the patient either voluntarily or involuntarily will be countered by the elastic bias of elastic band 16 interconnected between right cuff assembly 12 and left cuff assembly 14. Depending upon the size of the patient and/or the inherent strength of the patient, an elastic band may be constructed so as to have lesser or greater elastic strength. Conversely, when attempting to ambulate these patients and/or facilitate training, it may be preferable to use an elastic band with considerably less elastic strength as an accommodation to provide the patient greater mobility in extension and flexion of the hips in opposite directions with respect to each other as is accomplished in a walking gait.

The dynamic hip splint of the present invention accomplishes the much needed and desired repositioning of the legs of chronically disabled patients, providing the ability to place the legs into a more acceptable neutral positioning in relation to internal rotation and adduction of the lower extremities. This positioning is useful to facilitate delivering care, facilitating mobility, training, and improved gait control during ambulation training. A secondary desirable result is the improved alignment of the femoral head within the acetabulum during weight bearing which improves the forces delivered through the femur to the pelvis so as to be conducive toward improved hip growth and formation.

The foregoing is considered as illustrative only of the principles of the invention and since numerous modifications and changes will regularly occur to those skilled in the art, it is not desired to limit the invention to the exact construction and operation shown and described herein and accordingly, all suitable modifications and equivalents may be resorted to falling within the scope of the present invention.

I claim:

1. A dynamic hip splint for attaching to opposing thighs of a patient for correcting chronic abduction and external rotation of the patient's hips, the splint comprising:

a first thigh cuff having anterior posterior aspects suitably positionable in relation to an anterior and a posterior aspect of a thigh of the patient;

a second thigh cuff having anterior and posterior aspects suitably positionable in relation to an anterior and a posterior aspect of the opposite thigh of the patient; and an elastic band interconnecting between the first and second thigh cuffs adjacent at least the anterior aspects of the first and second thigh cuffs for urging the first and second thigh cuffs towards one another such that when the first and second thigh cuffs are positioned on a patient's thighs, the elastic band urging the first and second thigh cuffs towards each other results in adduction and internal rotation of the hips of the patient to a more neutral anatomic position.

2. The splint of claim 1 in which the first and second thigh cuffs include a resilient synthetic polymer.

3. The splint of claim 2 in which the resilient synthetic polymer includes a closed cell foam construction.

4. The splint of claim 1 in which the elastic band includes a rubber strand and fabric weave.

5. A dynamic hip splint for attaching to opposing thighs of a patient for correcting chronic abduction and external rotation of the patient's hips, the splint comprising:

a first adjustable thigh cuff and a second adjustable thigh cuff, each cuff positionable opposite the other on, and enclosable around, respective right and left thighs of the patient, and each cuff having two opposite free ends and a mid section therebetween, with each mid section positionable proximate the medial aspect of the respective thigh it encloses, the mid section of each cuff having a front portion and a back portion;

means for adjustably attaching the two free ends of each cuff to each other thereby enclosing each cuff around its respective thigh of the patient;

an elastic band, interconnecting between the first and second adjustable thigh cuffs for urging the first and second adjustable thigh cuffs towards one another, the elastic band having four limbs extending from a single locus, each limb having a free end, a first limb free end for attaching to the front portion of the first cuff, a second limb free end for attaching to the back portion of the first cuff, a third limb free end for attaching to the front portion of the second cuff, and a fourth limb free end for attaching to the back portion of the second cuff, and means for adjustably attaching the four limb free ends to each respective front and back portions such that when the first and second adjustable thigh cuffs are positioned on a patient's thighs, the elastic band urging the first and second adjustable thigh cuffs towards each other results in adduction and internal rotation of the hips of the patient to a more neutral anatomic position.

6. The splint of claim 5 in which the first and second thigh cuffs include a resilient synthetic polymer.

7. The splint of claim 6 in which the resilient synthetic polymer includes a closed cell foam construction.

8. The splint of claim 5 in which the elastic band includes a rubber strand and fabric weave.

9. The splint of claim 5 in which the means for adjustably attaching the two free ends of each cuff to each other includes a hook and loop material.

10. The splint of claim 5 in which the means for adjustably attaching the four limb free ends to each respective front and back portions includes a hook and loop material.

* * * * *

UNITED STATES PATENT AND TRADEMARK OFFICE
CERTIFICATE OF CORRECTION

PATENT NO. : 5,718,672
DATED : February 17, 1998
INVENTOR(S) : Lynda M. Woodman

It is certified that error appears in the above-indentified patent and that said Letters Patent is hereby corrected as shown below:

Col. 3, line 53, delete "prosthetic" and insert therefor --posterior--.

Col. 5, line 8, delete "or the patient,".

Col. 5, line 25, delete "&each" and insert therefor --of each--.

Signed and Sealed this

Fifth Day of May, 1998

Attest:

BRUCE LEHMAN

*Attesting Officer*               *Commissioner of Patents and Trademarks*